United States Patent
Sun et al.

(10) Patent No.: US 10,738,003 B2
(45) Date of Patent: Aug. 11, 2020

(54) PROCESS AND DEVICE FOR PREPARING ENVIRONMENTALLY-FRIENDLY INSULATING GAS PERFLUOROALKYLNITRILE

(71) Applicants: STATE GRID CORPORATION OF CHINA, Beijing (CN); STATE GRID SHAANXI ELECTRIC POWER RESEARCH INSTITUTE, Shaanxi (CN); CENTRAL SOUTH UNIVERSITY, Hunan (CN); STATE GRID (XI'AN) ENVIRONMENTAL PROTECTION TECHNIQUE CENTER CO. LTD, Shaanxi (CN)

(72) Inventors: Qiang Sun, Shaanxi (CN); Jian Wu, Shaanxi (CN); Yin Chen, Hunan (CN); De Ding, Shaanxi (CN); Genzhou Zhang, Shaanxi (CN); Xiaochun Bai, Shaanxi (CN); Anxiang Guo, Shaanxi (CN); Yantao Zhang, Shaanxi (CN); Pinghai Lv, Shaanxi (CN); Xiaobing Yu, Shaanxi (CN)

(73) Assignees: STATE GRID CORPORATION OF CHINA, Beijing (CN); STATE GRID SHAANXI ELECTRIC POWER RESEARCH INSTITUTE, Shaanxi (CN); CENTRAL SOUTH UNIVERSITY, Hunan (CN); STATE GRID (XI'AN) ENVIRONMENTAL PROTECTION TECHNIQUE CENTER CO. LTD, Shaanxi (CN)

( * ) Notice: Subject to any disclaimer, the term of this patent is extended or adjusted under 35 U.S.C. 154(b) by 0 days.

(21) Appl. No.: 16/616,670

(22) PCT Filed: Jan. 12, 2018

(86) PCT No.: PCT/CN2018/072314
§ 371 (c)(1),
(2) Date: Nov. 25, 2019

(87) PCT Pub. No.: WO2018/214519
PCT Pub. Date: Nov. 29, 2018

(65) Prior Publication Data
US 2020/0102265 A1 Apr. 2, 2020

(30) Foreign Application Priority Data
May 24, 2017 (CN) .......................... 2017 1 0375592

(51) Int. Cl.
*C07C 253/00* (2006.01)

(52) U.S. Cl.
CPC .................................. *C07C 253/00* (2013.01)

(58) Field of Classification Search
CPC .................................................... C07C 253/00
See application file for complete search history.

(56) References Cited

FOREIGN PATENT DOCUMENTS

CN          1048544 A          1/1991

OTHER PUBLICATIONS

Chambers et al. "Reactions involving fluoride ion. Part 401. Amines as initiators of fluoride ion catalysed reactions" Tetrahedron, 1995, vol. 51, No. 48, pp. 13167-13176.*
Chambers et al., "Reactions Involving Flouride Ion. Part 40. Amines as Initiators of Fluoride Ion Catalysed Reactions" Tetrahedron, 51 (48), Dec. 31, 1995, pp. 13167-13176, p. 13170, and p. 13174, paragraph 3.
Barlow et al., "Heterocyclic Polyfluoro-compounds. Part 30. Perfluoroalkylation of Trifluoro-1,2,4- triazine" Journal of the Chemical Society, Perkin Transactions 1: Organic and Bio-Organic Chemistry, vol. 10, Jan. 1, 1980, pp. 2254-2257, p. 2255.
Maxwell et al ., "The Indirect Fluorination of Cyanuric Chloride" Journal of the American Chemical Society, vol. 80, Feb. 5, 1958, pp. 548-549, p. 548.
Schroeder et al., "Synthesis of polyfluorinated heterocycles by indirect fluorination with silver fluorides. II. Fluoropyrimidines" Journal of Organic Chemistry, vol. 27, Jul. 31, 1962, pp. 2580-2584 and p. 2582.
International Search Report for the International Patent Application No. PCT/CN2018/072314, dated Apr. 20, 2018, 6 pages.

* cited by examiner

*Primary Examiner* — Joseph R Kosack

(57) ABSTRACT

Provided are a process and a device for preparing environmentally-friendly insulating gas perfluoroalkylnitrile. The device comprises a first tank reactor, a second tank reactor, and a fixed bed reactor. A condensing and collecting device is provided at the top of the first tank reactor, a collecting and guiding channel at the bottom of the condensing and collecting device is connected to an inlet of a storage tank, and an outlet of the storage tank is connected to an inlet of the second tank reactor. The second tank reactor is connected to a perfluoroolefin tank. An outlet of the second tank reactor is connected to a storage gasification tank. The storage gasification tank is connected to a carrier gas tank, and an outlet of the storage gasification tank is connected to an inlet of the fixed bed reactor. The present invention starts from cyanuric chloride and perfluoropropylene, and uses two tank reactors and a fixed bed reactor to realize production with high atom economy. The preparation method has simple reaction conditions, high atom economy, low cost, and is continuous and enables scale production.

8 Claims, 1 Drawing Sheet

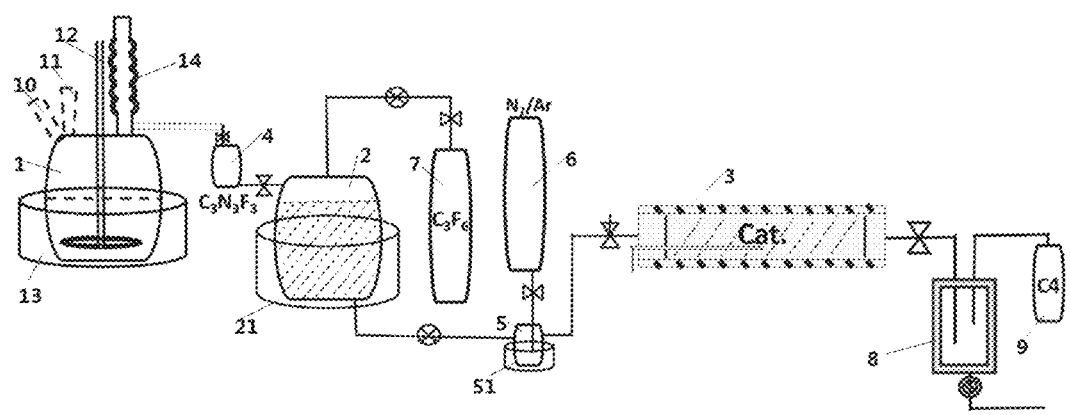

PROCESS AND DEVICE FOR PREPARING ENVIRONMENTALLY-FRIENDLY INSULATING GAS PERFLUOROALKYLNITRILE

CROSS-REFERENCE TO RELATED APPLICATIONS

This is a National Stage Application, filed under 35 U.S.C. 371, of International Patent Application No. PCT/CN2018/072314, filed on Jan. 12, 2018, which claims priority to Chinese patent application No. 201710375592.9 filed on May 24, 2017, contents of both of which are incorporated herein by reference in their entireties.

TECHNICAL FIELD

The present application relates to the technical field of insulating gases, in particular to a process and a device for preparing environmentally-friendly insulating gas perfluoroalkyl nitrile.

BACKGROUND

In recent years, with the development of social economy and the increase of world population, the large-scale use of fossil fuels and human activities allow the emission of various greenhouse gases to cause global accelerated warming, posing huge ecological and environmental problems. The greenhouse effect of sulfur hexafluoride insulating gas which is widely applied in the electric-power industry at present is nearly 20 thousand times of that of carbon dioxide. In order to avoid the use of such greenhouse gases, reduce the damage to the atmospheric ozone layer, and protect the natural environment on which human beings depend for survival, higher requirements are placed on insulating gases. Due to good inertness, high electrical insulation, very low degradation time in the atmospheric environment and greenhouse effect, perfluorotetracarbon nitrile is regarded as a new generation of environmentally-friendly insulating gas which can replace $SF_6$ following $CF_4$ and $C_2F_6$, and is widely concerned.

SUMMARY

The following is a brief summary of the subject matter that is described in greater detail herein. The summary is not intended to limit the protection scope of the claims.

The purpose of the present application is to provide a process and a device for preparing environmentally-friendly insulating gas perfluoroalkyl nitrile, which have simple reaction conditions, high atom economy, low cost, continuity and easy scale production.

To achieve this purpose, the present application adopts the following technical solutions:

The present application provides a device for preparing perfluoroalkyl nitrile, comprising a first tank reactor, a second tank reactor and a fixed bed reactor; a condensing and collecting device is provided at the top end of the first tank reactor, a collecting and diversion trench at the bottom of the condensing and collecting device is connected to an inlet of a material storage tank, and an outlet of the material storage tank is connected to an inlet of the second tank reactor; the second tank reactor is connected to a perfluoroolefin tank; an outlet of the second tank reactor is connected to a storage gasification tank; the storage gasification tank is connected to a carrier gas tank, and an outlet of the storage gasification tank is connected to an inlet of the fixed bed reactor.

Optionally, an outlet of the fixed bed reactor is connected to a perfluoroalkyl nitrile collecting tank via a gas purifier.

Optionally, the first tank reactor is equipped with a helical stirring device, a temperature control device and a continuous feed inlet which is sealable.

Optionally, the first tank reactor contains sulfolane, dimethylsulfoxide, DMF, NMP or other high-polarity aprotic solvents.

Optionally, the second tank reactor uses NaF, KF, CsF, AgF or other fluorides, or activated carbon-loaded NaF, KF, CsF, AgF or other fluorides (with a load amount of 10-40%); alternatively resins, silicon dioxide, alumina or other loading agents with trimethylamine, N-methylmorpholine or DABCO grafted on the surface as a catalyst.

Optionally, the fixed bed reactor is operated either with a catalyst comprising silica, platinum filament, activated carbon-loaded platinum or palladium, or without a catalyst.

The present application further provides a process for preparing environmentally-friendly insulating gas perfluoroalkyl nitrile, comprising the following steps: cyanuric chloride is reacted with sodium fluoride in sulfolane, dimethyl sulfoxide, DMF, DMP or other high-polarity aprotic solvents in the first tank reactor, and after condensation, the reaction product is fed into the second tank reactor for catalytic addition with perfluoroolefin under the action of a catalyst to generate trisperfluoroalkyl triazine; the trisperfluoroalkyl triazine is fed into the storage gasification tank and is carried into the fixed bed reactor by a carrier gas for further high-temperature catalytic cracking to obtain perfluoroalkyl nitrile.

Optionally, the molar ratio of cyanuric chloride to sodium fluoride in the first tank reactor is 1:(3-10), and the reaction temperature is 80-160° C.; the molar ratio of cyanuric fluoride to perfluoroolefin in the second tank reactor is 1:(3-8), the reaction temperature is 80-220° C., the reaction time is 2-60 h, and the reaction pressure is 1.2-20 Bar; and the reaction temperature in the fixed bed reactor is 400-1000° C.

Optionally, the second tank reactor uses NaF, KF, CsF, AgF or other fluorides, or activated carbon-loaded NaF, KF, CsF, AgF or other fluorides (with a load amount of 10-40%); alternatively resins, silicon dioxide, alumina or other loading agents with trimethylamine, N-methylmorpholine or DABCO grafted on the surface as a catalyst.

Optionally, the fixed bed reactor is operated either with a catalyst comprising silica, platinum filament, activated carbon-loaded platinum or palladium, or without a catalyst.

As compared to the existing technologies, the present application has the following beneficial effects: The present invention starts with cyanuric chloride and perfluoroolefin, through two tank reactors and one fixed bed reactor, to realize production with high atom economy. The preparation method has simple reaction conditions, high atom economy, low cost, continuity, easy scale production and a reaction yield of more than 97.1%.

BRIEF DESCRIPTION OF THE DRAWINGS

FIG. 1 is a schematic structural diagram of a device for preparing perfluoroalkyl nitrile according to an example of the present application.

DETAILED DESCRIPTION

The present application will be described in further detail below with reference to production examples, and modifications and variations made by those skilled in the relevant art based on the basic concept of the present application are all within the scope of the present application.

Referring to what are shown in FIG. 1, the present application provides a device for preparing perfluoroalkyl nitrile, comprising a first tank reactor 1 capable of continuous production, a second tank reactor 2 capable of continuous production, and a fixed bed reactor 3.

The first tank reactor 1 is equipped with two sealable continuous feed inlets 10 and 11 for feeding cyanuric chloride and sodium fluoride respectively; the first tank reactor 1 is provided with a spiral stirring device 12 and a temperature control device 13, the top end of the reactor is provided with a condensing and collecting device 14. Cyanuric chloride is reacted with sodium fluoride in sulfolane, dimethyl sulfoxide, DMF, NMP or other high-polarity aprotic solvents at a reaction temperature of 80-108° C., after condensation, the reaction product is fed into a collecting and diversion trench at the bottom of the condensing and collecting device 14 and is fed into a material storage tank 4. An outlet of the material storage tank 4 is connected to an inlet of the second tank reactor 2; the second tank reactor 2 is connected to a perfluoroolefin tank 7; an outlet of the second tank reactor 2 is connected to a storage gasification tank 5. After a plurality of equivalents of perfluoroolefin is introduced in the second tank reactor 2, catalytic addition is conducted under the action of a catalyst in the reactor to generate triperfluoroalkyl triazine, and the triperfluoroalkyl triazine is fed into the storage gasification tank 5 via a material outlet at the bottom of the second tank reactor 2. The storage gasification tank 5 is provided with a heater 51; the storage gasification tank 5 is connected to a carrier gas tank 6, and an outlet of the storage gasification tank 5 is connected to an inlet of the fixed bed reactor 3. The triperfluoroalkyl triazine in the storage gasification tank 5 is carried into the fixed bed reactor 3 by a carrier gas for further high-temperature catalytic cracking to obtain a perfluoroalkyl nitrile product. An outlet of the fixed bed reactor 3 is connected to a perfluoroalkyl nitrile collecting tank 9 via a gas purifier 8.

The tank reactors (e.g., the first tank reactor 1 and the second tank reactor 2), the fixed bed reactor 3, and the reactors having similar functions have been made of a metal material having good corrosion resistance and thermal conductivity, such as stainless steel or nickel alloy.

The second tank reactor 2 uses activated carbon-loaded (or unloaded) NaF, KF, CsF, AgF or other fluorides as a catalyst, with a catalyst load amount being 10-40% (Cat. 1) (Catalyst 1). Preparation of Cat. 1: NaF, KF, CsF, AgF or the like is weighted to prepare an aqueous solution with a concentration of 0.2-2 mol/l, activated carbon is added therein in proportion, following stirring for 0.5-3 h, the solvent is removed by a rotary evaporator, and drying under reduced pressure is conducted till constant weight, thus Cat. 1 is obtained.

The fixed bed reactor 3 is operated either with silica, platinum filament, activated carbon-loaded platinum or palladium the as a catalyst, or without a catalyst.

Example 1

The first tank reactor 1 has a volume of 20 L. 10 L of sulfolane, 3.7 Kg of cyanuric chloride and 4 Kg of NaF were respectively added into the first tank reactor 1 via the feed inlet. The materials were violently stirred at 150° C. for reaction, and the reaction product cyanuric fluoride continuously flew from the condensing and collecting device 14 to the material storage tank 4. When the outflow speed of the cyanuric fluoride became slow, cyanuric chloride and NaF were continued to be supplemented. When the materials in the first tank reactor 1 were too many and difficult to stir, the salt slurry at the bottom layer was pumped out, and the sulfolane was recycled and added into the first tank reactor 1 for continued use. The comprehensive yield of the reaction was 97%.

Example 2

The first tank reactor 1 has a volume of 20 L. 10 L of N,N-dimethylformamide, 3.7 Kg of cyanuric chloride and 5 Kg of NaF were respectively added into the first tank reactor 1 via the feed inlet. The materials were violently stirred at 150° C. for reaction, and the reaction product cyanuric fluoride continuously flew from the condensing and collecting device 14 to the material storage tank 4. When the outflow speed of the cyanuric fluoride became slow, cyanuric chloride and NaF were continued to be supplemented. When the materials in the first tank reactor 1 were too many and difficult to stir, the salt slurry at the bottom layer was pumped out, and the N,N-dimethylformamide was recycled and added into the first tank reactor 1 for continued use. The comprehensive yield of the reaction was 91%.

Example 3

The second tank reactor 2 has a volume of 100 L. Activated carbon-loaded 20% cesium fluoride was used as a catalyst, and the filling proportion of the catalyst in the reactor was 70% (70 L). Cyanuric fluoride (0.4 kilogram) and hexafluoropropylene (1.5 kilogram) were added into the second tank reactor 2 via a feed pipeline, with a reaction pressure being 3-7 bar and a reaction temperature being 140° C. After the pressure of the second tank reactor 2 was reduced during the reaction, an appropriate amount of hexafluoropropylene could be supplemented to maintain the pressure of the reaction system. After 20-80 hours of reaction, the reactor was cooled, and the reaction product trisperfluoroisopropyl triazine was fed into the storage gasification tank 5 via a discharge pipe at the bottom to be collected. The yield was 89%.

Example 4

The second tank reactor 2 has a volume of 100 L. Activated carbon-loaded 20% cesium fluoride was used as a catalyst, and the filling proportion of the catalyst in the reactor was 70% (70 L). Cyanuric fluoride (0.4 kilogram) and tetrafluoroethylene (1.0 kilogram) were added into the second tank reactor 2 via a feed pipeline, with a reaction pressure being 3-7 bar and a reaction temperature being 140° C. After the pressure of the second tank reactor 2 was reduced during the reaction, an appropriate amount of tetrafluoroethylene could be supplemented to maintain the pressure of the reaction system. After 20-80 hours of reaction, the reactor was cooled, and the reaction product trisperfluoroethyl triazine was fed into the storage gasification tank 5 via a discharge pipe at the bottom to be collected. The yield was 91%.

Example 5

The second tank reactor 2 has a volume of 100 L. Activated carbon-loaded 10% NaF was used as a catalyst, and the filling proportion of the catalyst in the reactor was 70% (70 L). Cyanuric fluoride (0.5 kilogram) and hexafluoropropylene (2.0 kilogram) were added into the second tank reactor 2 via a feed pipeline, with a reaction pressure being 3-9 bar and a reaction temperature being 140° C. After the pressure of the second tank reactor 2 was reduced during the reaction, an appropriate amount of hexafluoropropylene could be supplemented to maintain the pressure of the reaction system. After 20-80 hours of reaction, the reactor was cooled, and the reaction product trisperfluoroisopropyl triazine was fed into the storage gasification tank 5 via a discharge pipe at the bottom to be collected. The yield was 86%.

Example 6

The second tank reactor 2 has a volume of 100 L. Alumina with —$OCH_2CH_2NMe_2$ grafted on the surface was used as a catalyst, and the filling proportion of the catalyst in the reactor was 70% (70 L). Cyanuric fluoride (0.6 kilogram) and hexafluoropropylene (2.4 kilogram) were added into the second tank reactor 2 via a feed pipeline, with a reaction pressure being 3-7 bar and a reaction temperature being 120° C. After the pressure of the second tank reactor 2 was reduced during the reaction, an appropriate amount of hexafluoropropylene could be supplemented to maintain the pressure of the reaction system. After 20-40 hours of reaction, the reactor was cooled, and the reaction product trisperfluoroisopropyl triazine was fed into the storage gasification tank 5 via a discharge pipe at the bottom to be collected. The yield was 93%.

Example 7

The trisperfluoroisopropyl triazine was heated and gasified in the storage gasification tank 5 by a heater 51, and was carried into the fixed bed reactor 3 by a diluting carrier gas nitrogen or argon. The fixed bed reactor 3 is 80 cm long, and the pipe diameter is 2 inches. The reaction temperature was 550° C., activated carbon-loaded platinum was used as a catalyst, and the material contact time was 20-60 s. The product flowing out of the fixed bed reactor 3 was perfluoroisobutyl nitrile, and the yield of the reaction was 97.1%. The perfluoroisobutyl nitrile was obtained through purification and impurity removal by a gas purifier 8.

Example 8

The trisperfluoroisopropyl triazine was heated and gasified in the storage gasification tank 5 by a heater 51, and was carried into the fixed bed reactor 3 by a diluting carrier gas nitrogen or argon. The fixed bed reactor 3 is 80 cm long, and the pipe diameter is 2 inches. The reaction temperature was 680° C., silicon dioxide was used as a catalyst, and the material contact time was 20-60 s. The product flowing out of the fixed bed reactor 3 was perfluoroisobutyl nitrile, and the yield of the reaction was 91.4%. The perfluoroisobutyl nitrile was obtained through purification and impurity removal by a gas purifier 8.

What is claimed is:

1. A process for preparing environmentally-friendly insulating gas perfluoroalkyl nitrile, characterized by comprising: cyanuric chloride and sodium fluoride are subjected to fluorination reaction to generate cyanuric fluoride, then the cyanuric fluoride and perfluoroolefin are subjected to catalytic addition to generate trisperfluoroalkyl triazine, and the trisperfluoroalkyl triazine is carried into a fixed bed reactor by a carrier gas for high-temperature catalytic cracking to obtain the perfluoroalkyl nitrile.

2. The process for preparing environmentally-friendly insulating gas perfluoroalkyl nitrile according to claim 1, characterized in that the fluorination reaction occurs in sulfolane, dimethyl sulfoxide, DMF, DMP or other high-polarity aprotic solvents.

3. The process for preparing environmentally-friendly insulating gas perfluoroalkyl nitrile according to claim 1, characterized in that the catalyst used for the catalytic addition of cyanuric fluoride and perfluoroolefin to generate trisperfluoroalkyl triazine is as follows: 5-20 wt % of NaF, KF, CsF, AgF or other fluorides, 0.1-2 wt % of tertiary amine, or 30-90 wt % of resins or other loading agents with tertiary amine, N-methylmorpholine or DABCO grafted on the surface.

4. The process for preparing environmentally-friendly insulating gas perfluoroalkyl nitrile according to claim 1, characterized in that the trisperfluoroalkyl triazine is subjected to gasification and carried into a fixed bed reactor by a carrier gas for high-temperature catalytic cracking to obtain perfluoroalkyl nitrile, wherein the catalyst used in the fixed bed reactor is a metal salt loaded by a loading agent of alumina, molecular sieve, activated carbon, phosphomolybdic acid, or phosphotungstic acid.

5. The process for preparing environmentally-friendly insulating gas perfluoroalkyl nitrile according to claim 4, characterized in that the metal salt is platinum, palladium or copper salt.

6. The process for preparing environmentally-friendly insulating gas perfluoroalkyl nitrile according to claim 4, characterized in that the metal salt is copper nitrate, palladium chloride or chloroplatinic acid.

7. The process for preparing environmentally-friendly insulating gas perfluoroalkyl nitrile according to claim 4, characterized in that the loading agent is phosphomolybdic acid or phosphotungstic acid.

8. The process for preparing environmentally-friendly insulating gas perfluoroalkyl nitrile according to claim 1, characterized in that the molar ratio of cyanuric chloride to sodium fluoride in the fluorination reaction is 1:(3-10), and the reaction temperature is 80-160° C.; the molar ratio of cyanuric fluoride to perfluoroolefin in the catalytic addition is 1:(3-8), the reaction temperature is 80-220° C., the reaction time is 2-60 h, and the reaction pressure is 1.2-20 Bar; and the reaction temperature in the high-temperature catalytic cracking is 400-1000° C.

* * * * *